United States Patent
Konesky

(10) Patent No.: US 7,316,682 B2
(45) Date of Patent: Jan. 8, 2008

(54) ELECTROSURGICAL DEVICE TO GENERATE A PLASMA STREAM

(75) Inventor: Gregory A. Konesky, Hampton Bays, NY (US)

(73) Assignee: Aaron Medical Industries, Inc., St. Petersburg, FL (US)

( * ) Notice: Subject to any disclaimer, the term of this patent is extended or adjusted under 35 U.S.C. 154(b) by 686 days.

(21) Appl. No.: 10/321,947

(22) Filed: Dec. 17, 2002

(65) Prior Publication Data

US 2004/0116918 A1  Jun. 17, 2004

(51) Int. Cl.
*A61B 18/18* (2006.01)
(52) U.S. Cl. .......................... 606/40; 606/49
(58) Field of Classification Search ................. 606/34, 606/37, 39–42, 45, 27, 46–50
See application file for complete search history.

(56) References Cited

U.S. PATENT DOCUMENTS

| 3,601,126 | A | * | 8/1971 | Estes | 606/35 |
| 4,060,088 | A | * | 11/1977 | Morrison et al. | 606/49 |
| 5,776,092 | A | * | 7/1998 | Farin et al. | 604/22 |
| 6,213,999 | B1 | * | 4/2001 | Platt et al. | 606/27 |
| 6,852,112 | B2 | * | 2/2005 | Platt | 606/49 |
| 2005/0234442 | A1 | * | 10/2005 | Spears | 606/39 |

* cited by examiner

Primary Examiner—Michael Peffley
(74) Attorney, Agent, or Firm—Arthur W. Fisher, III

(57) ABSTRACT

An electrosurgical device to generate a plasma stream for performing electrosurgery on a surgical site on a patient comprising an electrosurgical generator coupled to a electrical power source to supply power to the electrosurgical device and a plasma generator including an electrode operatively coupled to the electrosurgical generator to receive electrical energy therefrom and concentrically disposed within an inner noble gas conduit to form a plasma channel coupled to a noble gas source to feed noble gas to the inner noble gas conduct, an intermediate electronegative gas conduit disposed in surrounding coaxial relation relative to the noble gas conduit to cooperatively form an electronegative gas channel therebetween coupled to a gas source to feed electronegative gas to the electronegative gas channel and an outer aspiration conduit disposed in surrounding coaxial relation relative to the intermediate electronegative gas conduit to cooperatively form an aspiration channel therebetween coupled to a negative pressure source such that the electrode heats the noble gas to at least partially ionize the noble gas to generate the plasma stream to be directed to the surgical site to perform the surgical procedure while the electronegative gas maintains or sustains the plasma stream and the negative pressure source removes fluid and solid debris from the surgical site.

6 Claims, 8 Drawing Sheets

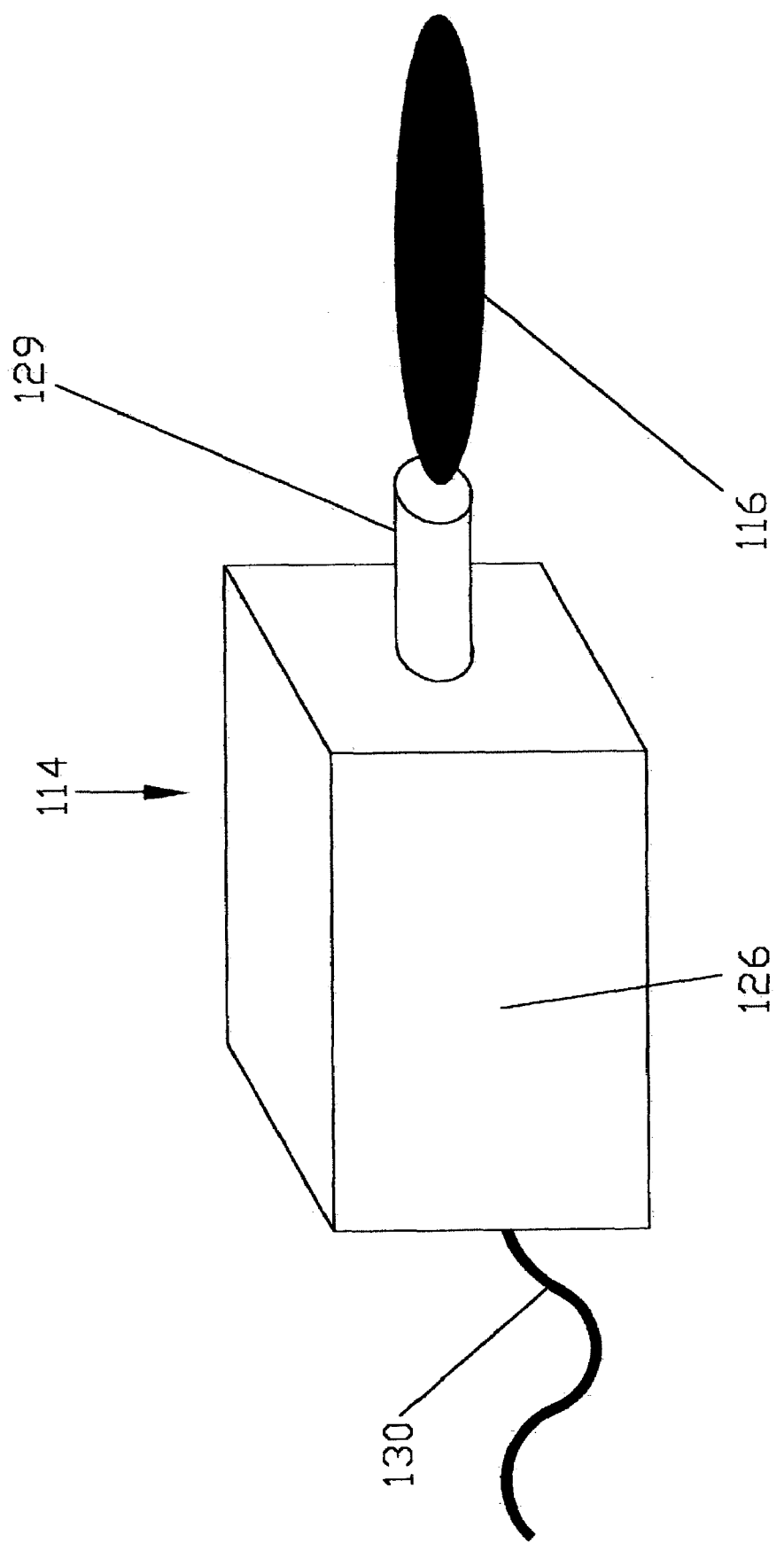

ELECTROSURGICAL DEVICE TO GENERATE A PLASMA STREAM

BACKGROUND OF THE INVENTION

1. Field of the Invention

An electrosurgical device to generate a plasma stream to perform electrosurgery on a surgical target area on a patient.

2. Description of the Prior Art

High frequency electrical energy has been widely used in surgery. Tissue is cut and bodily fluids are coagulated using electrosurgical energy.

Electrosurgical instruments generally comprise "monopolar" devices or "bipolar" devices. Monopolar devices comprise an active electrode on the electrosurgical instrument with a return electrode attached to the patient. In monopolar electrosurgery, the electrosurgical energy flows through the active electrode on the instrument through the patient's body to the return electrode. Such monopolar devices are effective in surgical procedures where cutting and coagulation of tissue are required and where stray electrical currents do not pose a substantial risk to the patient.

Bipolar devices comprise an active electrode and a return electrode on the surgical instrument. In a bipolar electrosurgical device, electrosurgical energy flows through the active electrode to the tissue of a patient through a short distance through the tissue to the return electrode. The electrosurgical effects are substantially localized to a small area of tissue that is disposed between the two electrodes on the surgical instrument. Bipolar electrosurgical devices have been found to be useful with surgical procedures where stray electrical currents may pose a hazard to the patient or where other procedural concerns require close proximity of the active and return electrodes. Surgical operations involving bipolar electrosurgery often require methods and procedures that differ substantially from the methods and procedures involving monopolar electrosurgery.

Gas plasma is an ionized gas capable of conducting electrical energy. Plasmas are used in surgical devices to conduct electrosurgical energy to a patient. The plasma conducts the energy by providing a pathway of relatively low electrical resistance. The electrosurgical energy will follow through the plasma to cut, coagulate, desiccate, or fulgurate blood or tissue of the patient. There is no physical contact required between an electrode and the tissue treated.

Electrosurgical systems that do not incorporate a source of regulated gas can ionize the ambient air between the active electrode and the patient. The plasma that is thereby created will conduct the electrosurgical energy to the patient, although the plasma arc will typically appear more spatially dispersed compared with systems that have a regulated flow of ionizable gas.

One of the difficulties in using a plasma is its initiation. A strong electrical field is required to accelerate enough free electrons within the gas such that a cascade of ionizing collisions is initiated which creates the plasma. This is sometimes called "igniting" the plasma. Once a plasma is ignited, it may be sustained at lower electrical field potentials.

Several techniques are presently used to create strong electrical fields that can ignite the plasma. One technique is to move the tip of an electrode very close to the surgical site. The electric field along a path between an electrode and the surgical site increases as their separation decreases, and may reach a level sufficient to ignite the plasma. The drawback of this method is that a surgeon must carefully manipulate the electrode to move it close to the surgical site without actually touching the tissue. If the electrode comes in contact with the tissue it may stick, causing eschar to deposit on the electrode. During laparoscopic procedures, it is often difficult for a surgeon to sense the proximity of the electrode to the tissue.

Another technique to ignite plasma is to use a pointed electrode which will generate a stronger electrical field at the tip of the electrode. However, a pointed electrode may be undesirable if the surgeon requires a blade-shaped electrode for cutting and other tissue manipulation. Yet another technique is to provide high voltage spikes to the surgical electrode until a detector has indicated a closed circuit with the return electrode. Once a closed circuit is detected, the high voltage spikes are terminated and the electrosurgical generator returns to its normal waveform output. While this technique is effective, it requires complicated electronics and components capable of withstanding the high voltages.

U.S. Pat. No. 4,060,088 relates to a monopolar electrosurgical method and apparatus for coagulation by fulguration. The apparatus has source of inert ionized gas which surrounds a tubular electrosurgical electrode. There is also disclosed a source of periodic bursts of electrosurgical energy used to initiate the plasma arc. Only one electrode is disclosed on the electrosurgical apparatus so that the device is monopolar.

U.S. Pat. No. 4,781,175 teaches the application of an ionizable gas jet to the tissue to clear bodily fluids and coagulate or achieve fulguration in the form of an improved eschar using an instrument having a conduit for the flow of gas at a predetermined flow rate about a centrally located electrode for electrosurgical energy. Circuitry and computer logic are shown to control the gas jet flow and the electrosurgical energy. No return path for the electrosurgical energy is provided.

U.S. Pat. Nos. 3,970,088, 3,987,795 and 4,043,342 describe sesquipolar electrodes on an instrument used to apply electrosurgical energy to an operative site.

U.S. Pat. No. 4,041,952 employs a switch on a forceps used as monopolar or bipolar during treatment of the patient with electrosurgery.

U.S. Pat. No. 4,890,610 discloses a pair of bipolar forceps comprising coined metallic conductive blades that are each over-molded with a plastic insulator to leave exposed tips at the patient end and connector terminals for electrosurgical energy at the opposite ends.

U.S. Pat. No. 4,492,231 teaches a bipolar circuit to provide non-stick coagulation by use of a good thermal conductor and minimal contact relative to the volume of conductive material in the tines of the forceps.

U.S. Pat. No. 4,060,088 relates to a monopolar electrosurgical unit in combination with an ionizable gas delivery system.

U.S. Pat. No. 4,040,426 shows a method and apparatus for initiating an electrical discharge in the ionizable gas.

U.S. Pat. No. 4,901,719 teaches a monopolar electrosurgical unit in combination with an ionizable gas delivery system including a gas conducting means.

U.S. Pat. No. 4,429,694 shows a solid-state electrosurgical generator which provides output waveforms that are optimized for electrosurgical fulguration. The fulguration output circuitry consists of a radio-frequency tank circuit which is periodically pulsed to produce a periodic damped-sinusoidal output waveform. However, the damping factor is sufficiently low so that many cycles of the waveform occur between periodic input pulses. Although the duty cycle is relatively high compared to prior art devices, cutting and burning effects are prevented by a high impedance output which internally limits fulguration arc current. The fulgurating arc developed by the device is longer and more consistent than that developed by previous devices thereby resulting in superior fulguration.

U.S. Pat. No. 4,901,720 discloses an electrosurgical generator in an electrosurgical unit (ESU) controls the repetition rate and the energy content of bursts of RF energy delivered to a gas jet supplied by the ESU, in order to maintain RF leakage current within acceptable limits while still achieving a sufficient state of ionization in the gas jet to reliably initiate the conduction of arcs to the tissue. The repetition rate of the RF bursts is substantially reduced in an inactive state when no arcs are delivered. A relatively small number of the RF bursts delivered during the inactive state have an increased or boosted energy content to assure an adequate ionization state in the gas jet.

U.S. Pat. No. 5,088,997 shows a device for enhancing the safety and efficiency of a hand-operated electrosurgical pencil having an electrode with a distal end defining a tip for cutting or coagulating biological tissue, which device comprises a nose piece adapted to be mounted about said electrode and containing conduit means defining converging pathways for streams of gas which impinge obliquely on said electrode at or near the tip thereof, and electrosurgical apparatus incorporating said device and a method for coagulating or cutting biological tissue using said apparatus.

U.S. Pat. No. 6,213,999 describes an apparatus and method for igniting plasma in a surgical system is disclosed. A corona discharge is generated on a surgical handpiece which is used to ignite a plasma arc for surgical operations. The advantages include greater reliability and repeatability of plasma arc ignition. The apparatus comprises a handpiece incorporating an active electrode, a passage for ionizable gas, and a corona return electrode. The corona return electrode has a terminus on the holder and near the distal end of the holder. The corona return electrode is electrically connected to the return path of the electrosurgical generator. A non-uniform electric field is generated between the active electrode and the corona return electrode of sufficient strength so that a corona is formed near the active electrode. A separate return electrode may be on the patient, or the apparatus may be configured for bipolar electrosurgical operation by carrying the return electrode on the handpiece. A dielectric material separates the active electrode and the corona return electrode. There is substantially capacitive coupling between the active electrode and the corona return electrode. There is substantially resistive coupling between the active electrode and the return electrode.

Additional examples of the prior art are found in U.S. Pat. Nos. 1,889,609; 2,835,254; 3,577,030; 3,949,266; 4,559,943; 4,818,916; 4,887,005; 5,302,881; 5,325,019; 5,669,904; 5,710,486; 5,717,293; 5,801,489; 5,815,047; 5,917,286; 6,046,546; 6,181,068; 6,222,321; and 6,262,538.

SUMMARY OF THE INVENTION

The present invention relates to an electrosurgical device to generate a plasma stream to perform electrosurgery on a surgical site on a patient.

The electrosurgical device comprises an electrosurgical generator coupled to an electrical power source to supply power for the electrosurgical device and a plasma generator including an electrode operatively coupled to the electrosurgical generator to selectively receive electrical energy therefrom and to generate the plasma stream.

An inner noble gas conduit coupled to a noble gas source to feed noble gas such as helium or argon to the noble gas conduit surrounds the electrode to at least partially ionize the noble gas to create the plasma stream. An intermediate electronegative gas conduit may be disposed in surrounding coaxial relation relative to the noble gas conduit is coupled to a gas source to feed electronegative gas or air such as oxygen and nitrogen to the intermediate electronegative gas conduit to maintain the plasma stream. Finally, an outer aspiration conduit maybe coupled to a negative pressure source such as a vacuum disposed in surrounding coaxial relation relative to the intermediate electronegative gas conduit to remove fluid and solid debris from the surgical site.

Oxygen and nitrogen in the atmosphere surrounding the plasma phase tend to act to confine the discharge to an elongated narrow beam. However, if plasma is applied to an internal cavity or endoscopically, the noble gas flow from the plasma stream displaces any air remaining within the cavity. In addition, the plasma stream is operated in a surrounding atmosphere, the plasma stream eventually discharges randomly. This is undesirable where precision pinpoint accuracy is required.

In order to maintain the profile of the plasma stream when used within a confined space, the intermediate electronegative gas conduit is employed. This intermediate electronegative gas conduit extends beyond the inner noble gas conduit in order to maintain a laminar coaxial flow.

Noble gas and air flow rates are generally equal. However, air flow rates in excess of the noble gas flow rate can be used to enhance flow-assisted removal of smoke and debris generated during the surgical procedure. Excessive flow rates of either noble gas or air can induce turbulence in the plasma stream and distort the discharge jet shape.

Gases other than air can be used in the intermediate electronegative gas conduit. Cross-boundary diffusion from the plasma stream into the surrounding air and air diffusion into the plasma stream limits the effective length of the plasma stream. By substituting additional noble gas flow for air in the intermediate electronegative gas conduit, a significantly extended plasma stream can be obtained. Reduced concentration gradient occur with the noble gas from the inner ionized jet diffusing into non-ionized noble gas in the outer coaxial flow and vice versa. This results in overall plasma stream that are between two and two and a half times as long as those without a coaxial noble gas flow under otherwise identical conditions.

Since the cross section area of a conduit scales with the square of the radius, the diameter of the outer aspiration conduit need not be excessive to accommodate both the inner noble gas conduit and the intermediate electronegative gas conduit. At the same time, the inside diameter of the outer aspiration conduit should be large enough to permit aspiration of fluid and debris generated during the surgical procedure. The length of the outer aspiration conduit should be shorter than the intermediate electronegative gas conduit. Otherwise, the air sheath is immediately aspirated and the benefit in confined spaces is compromised.

Saline solution may be intermittently substituted for the air flow to enhance debris removal. Plasma activation should be suspended during this phase or mode of the procedure.

The invention accordingly comprises the features of construction, combination of elements, and arrangement of parts that will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which:

FIG. 6 is a perspective view of the plasma generator of the electrosurgical device of the present invention.

Similar reference characters refer to similar parts throughout the several views of the drawings.

DETAILED DESCRIPTION OF THE PREFERRED EMBODIMENT

The present invention relates to an electrosurgical device. As described more fully hereinafter, the electrosurgical device comprises an electrosurgical generator to supply power to the electrosurgical device and a plasma generator operatively coupled to the electrosurgical generator to receive electrical power therefrom and to generate a plasma stream for application to a surgical site or target area on a patient.

Figure 1:
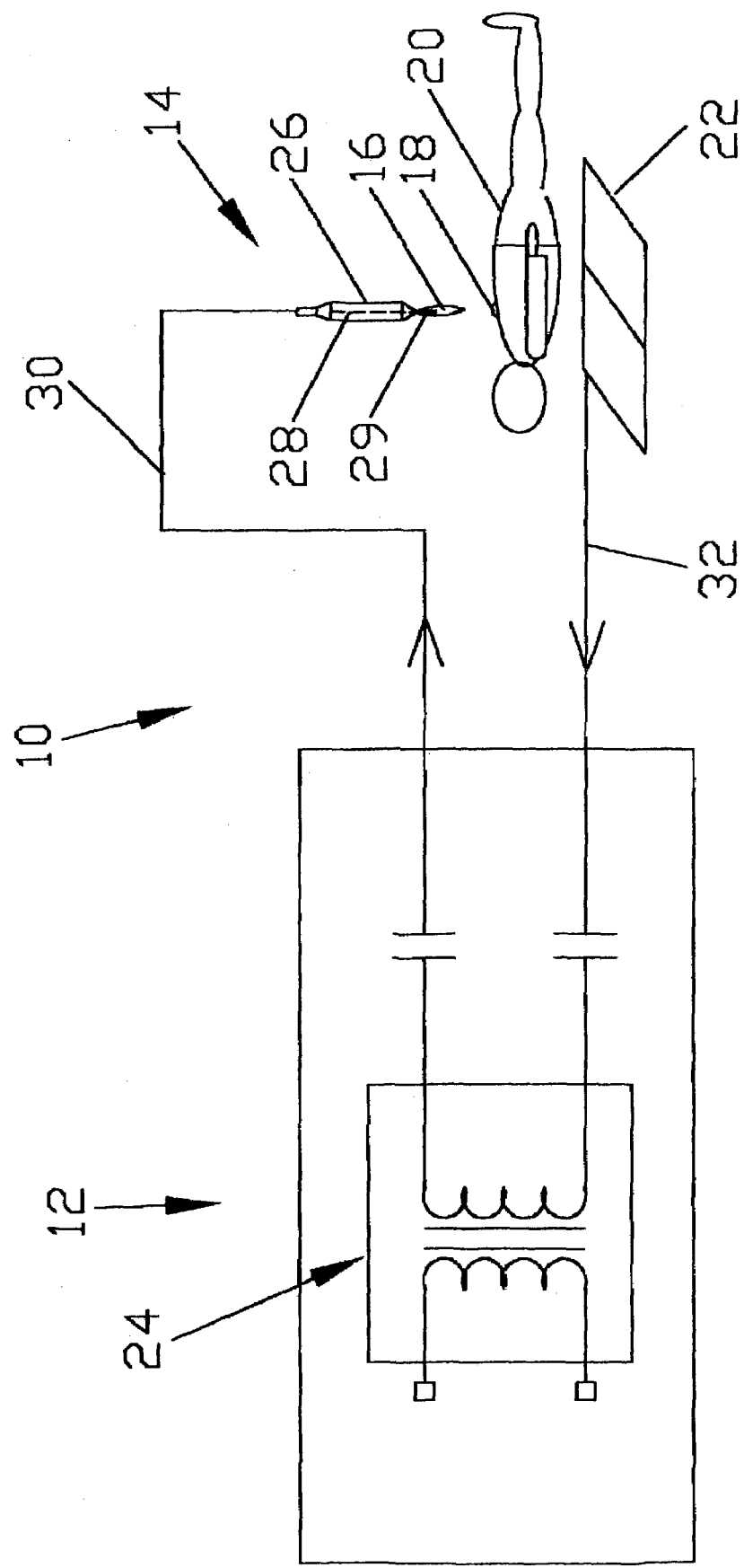
FIG. 1 is a schematic of a monopolar electrosurgical device and a patient.

FIG. 1 shows a prior art monopolar electrosurgical device generally indicated as 10 comprising an electrosurgical generator generally indicated as 12 to generate power for the electrosurgical device 10 and a plasma generator generally indicated as 14 to generate and apply a plasma stream 16 to a surgical site or target area 18 on a patient 20 resting on a conductive plate or support surface 22.

The electrosurgical generator 12 includes a transformer generally indicated as 24 including a primary and secondary coupled to an electrical source (not shown) to provide high frequency electrical energy to the plasma generator 14. Typically, the electrosurgical generator 12 comprises an isolated floating potential not referenced to any potential. Thus, current flows between the active and return electrodes. If the output is not isolated, but referenced to "earth", current can flow to areas with ground potential. If the contact surface of these areas and the patient is relatively small, an undesirable burning can occur.

The plasma generator 14 comprises a handpiece or holder 26 having an electrode 28 at least partially disposed within a fluid flow housing 29 and coupled to the transformer 24 to receive the high frequency electrical energy therefrom to at least partially ionize noble gas fed to the fluid flow housing 29 of the handpiece or holder 26 to generate or create the plasma stream 16.

The high frequency electrical energy is fed from the secondary of the transformer 24 through an active conductor 30 to the electrode 28 (collectively active electrode) in the handpiece 26 to create the plasma stream 16 for application to the surgical site 18 on the patient 20.

The return path to the electrosurgical generator 12 is through the tissue and body fluid of the patient 20, the conductor plate or support member 22 and a return conductor 32 (collectively return electrode) to the secondary of the transformer 24 to complete the isolated, floating potential circuit.

U.S. Pat. No. 6,213,999 discloses both monopolar and bipolar electrosurgical generators.

Figure 2:
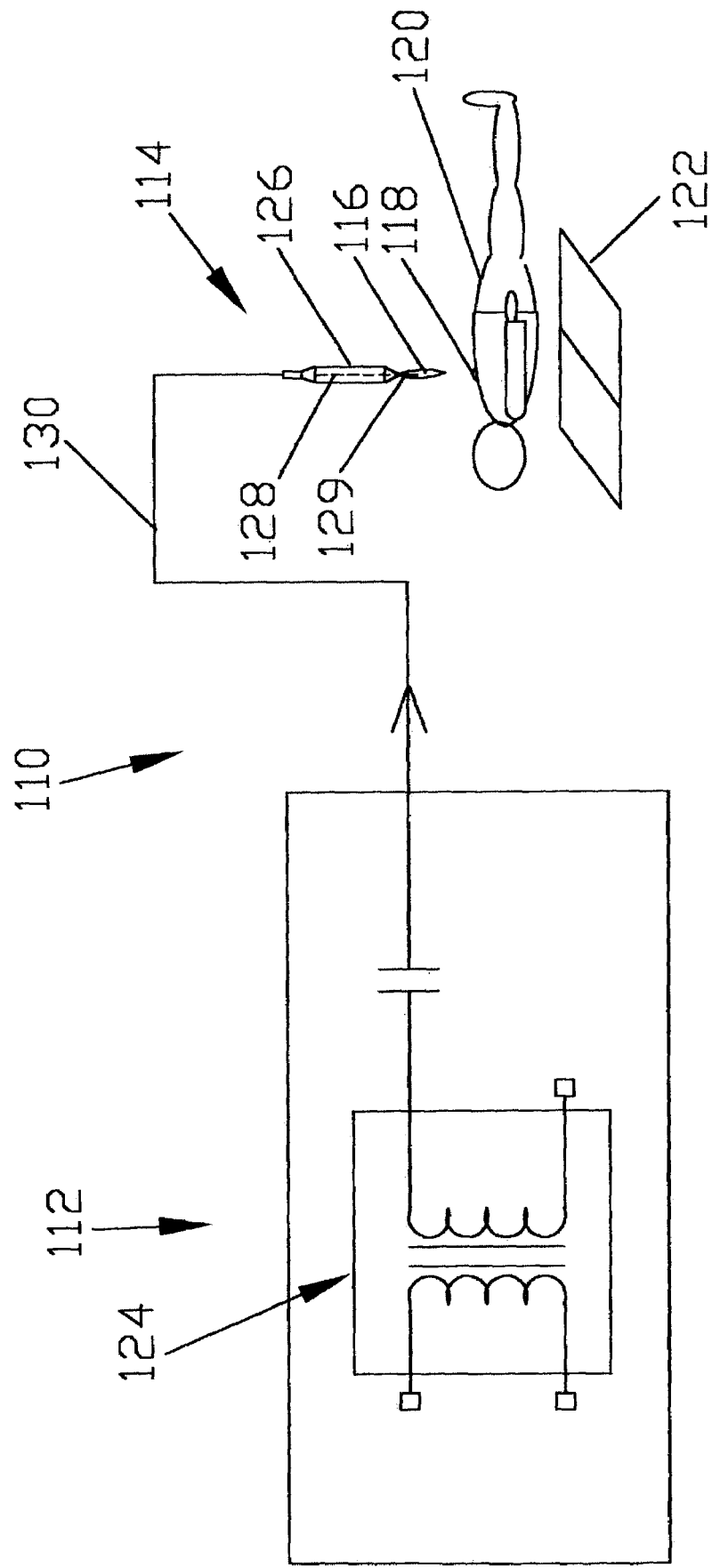
FIG. 2 is a schematic of the electrosurgical device of the present invention and a patient.

As shown in FIG. 2, the electrosurgical device 110 of the present invention comprises an electrosurgical generator generally indicated as 112 to generate power for the electrosurgical device 110 and a plasma generator 114 to generate and apply a plasma stream 116 to a surgical site or target area 118 on a patient 120 resting on a conductive plate or support element 122.

The electrosurgical generator 112 includes a transformer generally indicated as 124 including a primary and secondary coupled to an electrical source (not shown) to provide high frequency electrical energy to the plasma generator 114. Typically, the electrosurgical generator 112 comprises an isolated nonfloating potential not referenced to any potential.

The plasma generator 114 comprises a handpiece or holder 126 having an electrode 128 at least partially disposed within a fluid flow housing 129 and coupled to the transformer 124 to receive the high frequency electrical energy therefrom to at least partially ionize noble gas fed to the fluid flow housing 129 of the handpiece or holder 126 to generate or create the plasma stream 116.

The high frequency electrical energy is fed from the secondary of the transformer 124 through an active conductor 130 to the electrode 128 in the handpiece 126 to create the plasma stream 116 for application to the surgical site 118 on the patient 120.

The plasma current flow back to the electrosurgical generator 112 is through the tissue and body fluid and the patient 120. From there, the return current circuit is completed through the combined external capacitance to the plasma generator handpiece 124, surgeon and through displacement current in the air. The capacitance is determined, among other things, by the physical size of the patient 120.

Figure 3:
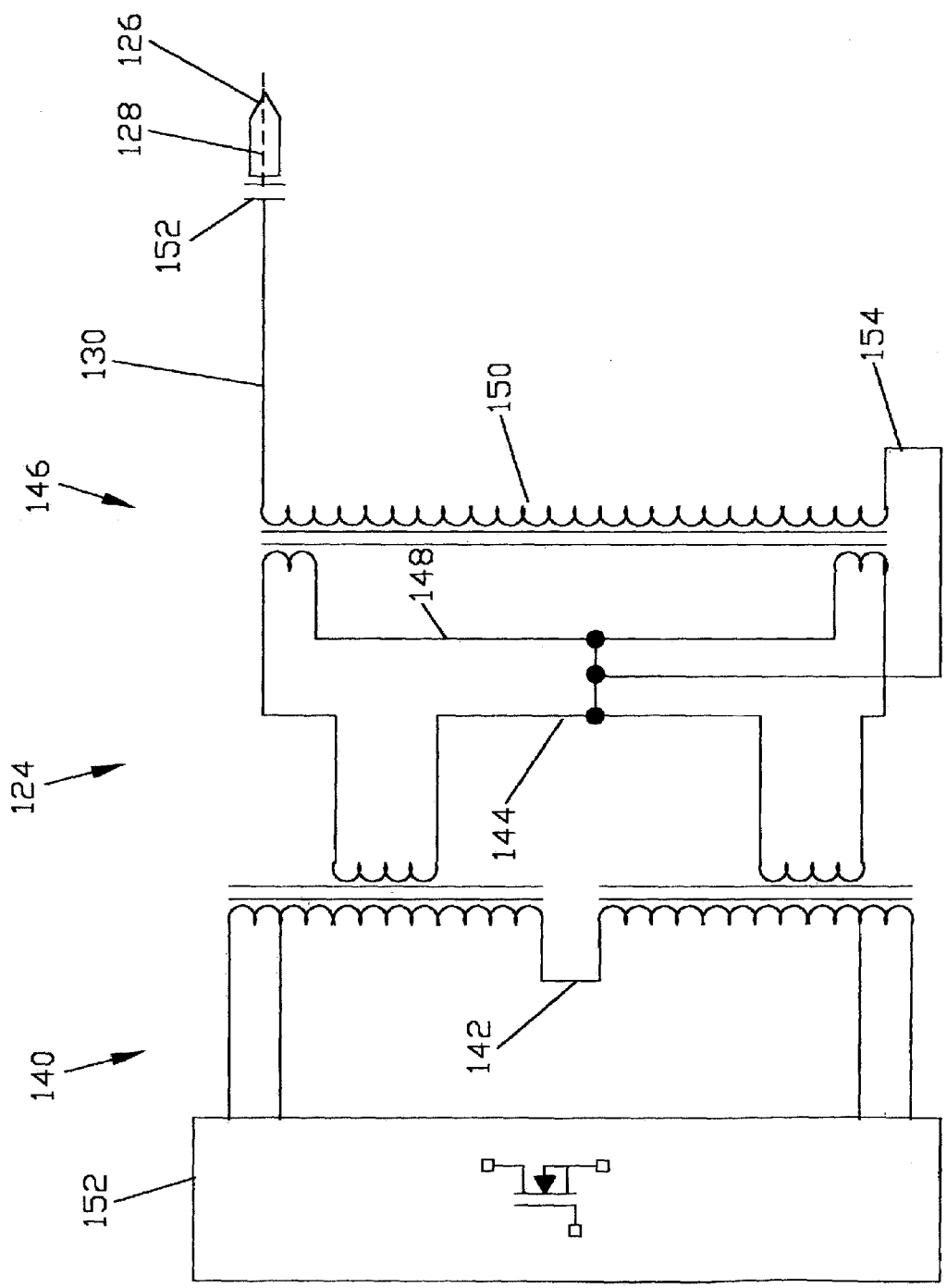
FIG. 3 is a detailed schematic of the isolated, non-floating transformer of the electrosurgical generator of the electrosurgical device of the present invention.

FIG. 3 shows the transformer 124 in detail. The transformer 124 comprises a step-down section or stage generally indicated as 140 including a primary 142 and secondary 144 and a step-up section or stage generally indicated as 146 including a primary 148 and secondary 150 operatively coupled together. The primary 142 of the step-down section or stage 140 is coupled across a power amplifier 152; while, the secondary 150 of the step-up section or stage 146 is coupled between the electrode 128 through the active conductor 130 and a series capacitor 152 and the isolated nonfloating return 154. The step-down, step-up configuration provides a fixed or constant potential (FIXEDPOT).

The series capacitor 152 is equal to or less than 20 Pf limiting the leakage current to a safe level below about 150 mA RMS. Compared to a typical load of from about fifty ohms, the Zc is relatively high. As a result, the current output of the plasma generator 114 is substantially constant. In addition, the transformer output has a substantial constant potential. The continuous output waveform has a crest factor of about 1.4-1.5. As a result, the ignition of the noble gas is relatively stable.

Thus, the plasma output is a relatively constant current source and the working currents do not exceed about 150 mA RMS. Here the leakage current is the functional current. Because the value of the current and crest-factor is low, but Vpp voltage—very high, the heat transfer in the tissue is very low, so undesired tissue damage is very low. Increasing the application time could compensate the insufficient heat transfer.

The plasma generator effect also depends on the shape of the electrode. If the electro-magnetic field in the "near zone" around the electrode tip is constant compared with the electromagnetic wave length (400 kHz), the EMF can be considered static. In that case, the ignition of the plasma depends on the so-called "electrostatic pressure", which is higher for sharper electrode shapes. Thus, the sharper and thinner the electrode is, the better initial (cold) plasma ignition. After the cold ignition the plasma beam is supported by the thermo electronic emission, which, due to the low current, is not as intensive as in the APC.

Figure 5:
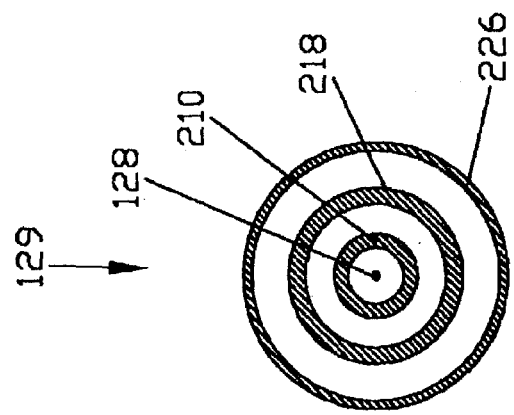
FIG. 5 is a cross sectional end view of the plasma generator of the electrosurgical device of the present taken along line 5-5 of FIG. 4.
Figure 4:
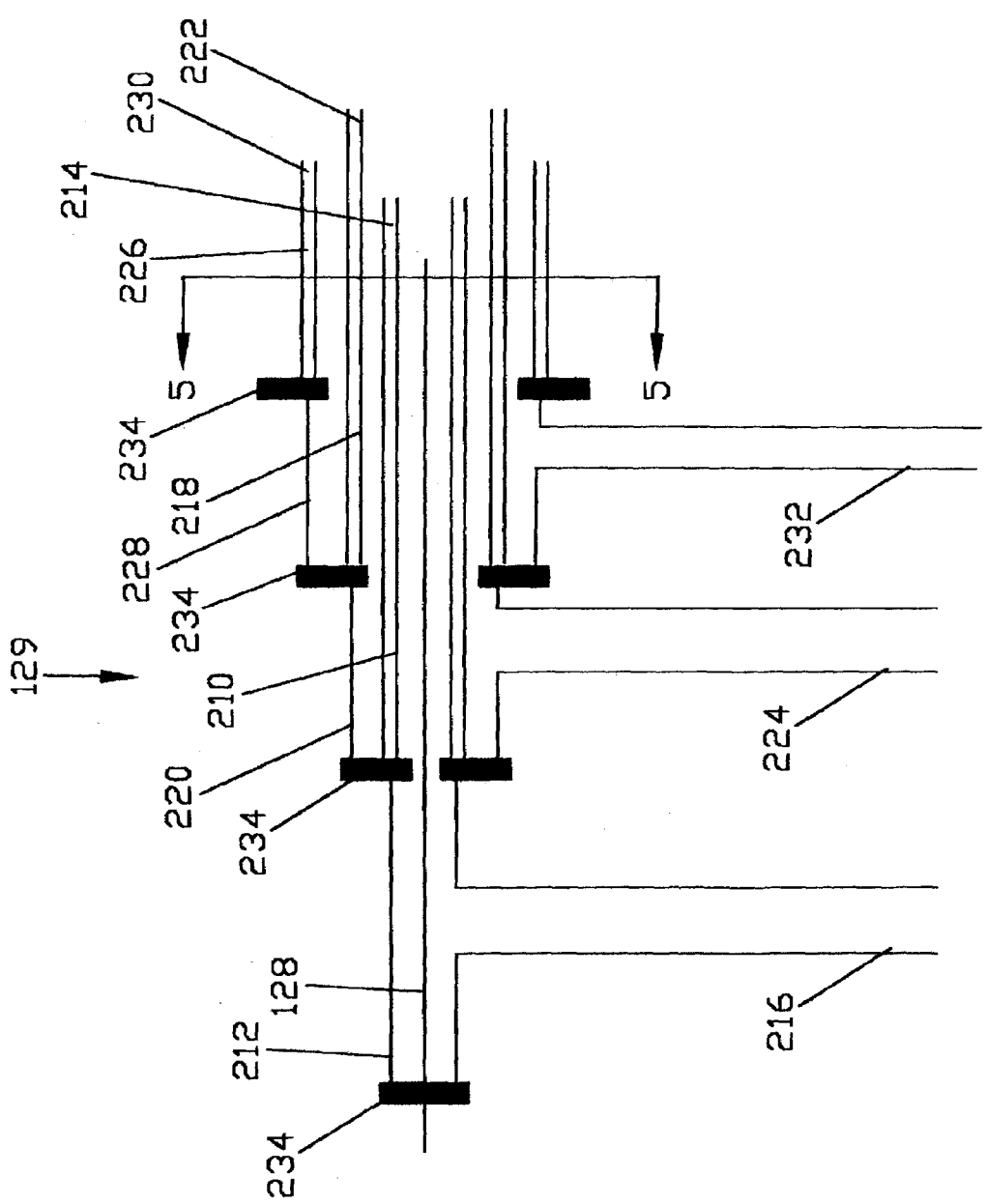
FIG. 4 is a partial diagrammatic side view of the plasma generator of the electrosurgical device of the present invention.

As best shown in FIGS. 4 and 5, the plasma generator 114 includes the electrode 128 supported by the handpiece 126 and at least partially disposed in the fluid flow housing 129. As previously described, the electrode 128 is operatively coupled to the electrosurgical generator 112 to selectively receive electrical energy therefrom. The electrode 128 is concentrically disposed within an inner noble gas conduit 210 having a proximal end 212 and a distal end 214 coupled to a noble gas source (not shown) by a noble gas supply conduit 216 to feed noble gas such as helium or argon to the noble gas conduct 210.

An intermediate air or electronegative gas conduit 218 is disposed in surrounding coaxial relation relative to the noble gas conduit 210 having a proximal end 220 and a distal end 222 coupled to a gas source (not shown) by an air or electronegative gas supply conduit 224 to feed air or electronegative gas such as oxygen and nitrogen to the intermediate air or electronegative gas conduit 218. The distal end 214 of the inner noble gas conduit 210 is disposed inwardly from the distal end 222 of the intermediate electronegative gas conduit 218. Alternately, in place of the air or electronegative gas, noble gas may be fed through the intermediate air or electronegative gas conduit 218 to create a diffuse cylindrically shaped relatively wide area plasma beam useful with particular procedures such as dermatology.

An outer aspiration conduit 226 is disposed in surrounding coaxial relation relative to the intermediate air or electronegative gas conduit 218 having a proximal end 228 and a distal end 230 coupled to a negative pressure source such as a vacuum (not shown) by a negative pressure conduit 232 to remove fluid and solid debris from the target area 118 on the patient 120. The distal end 230 of the outer aspiration conduit 226 is disposed inwardly from the distal end 222 of the intermediate air or electronegative gas conduit 218.

A plurality of seals each indicated as 234 are used to seal the noble gas conduit 210, the intermediate air or electronegative gas conduit 218 and the outer aspiration gas conduit 226.

Figure 10:
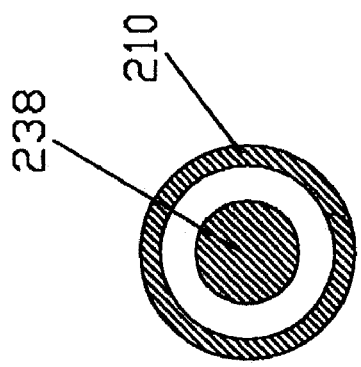
FIG. 10 is a cross sectional end view of the plasma generator of the electrosurgical device of the present invention taken along line 10 of FIG. 9.
Figure 9:
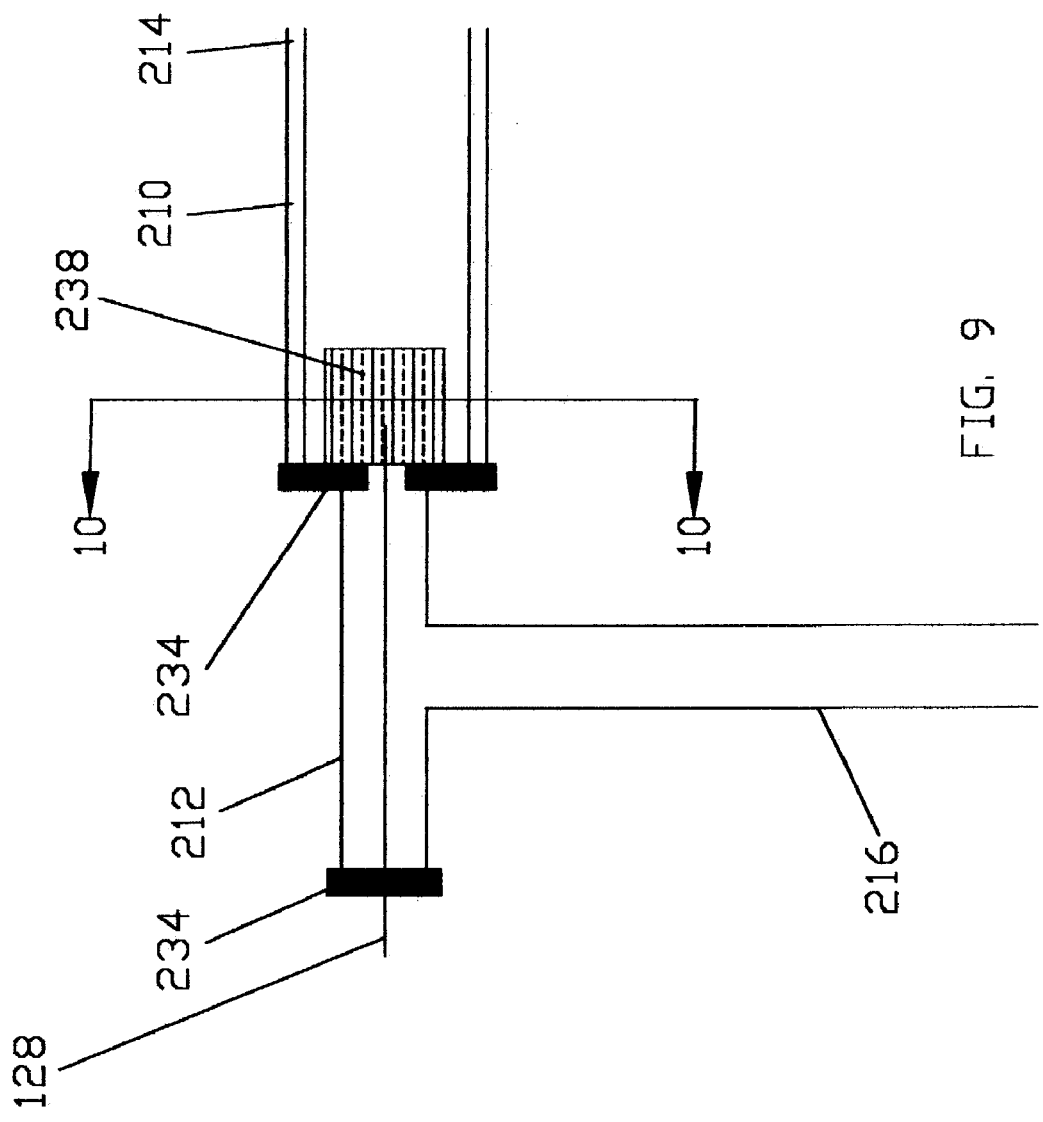
FIG. 9 is a partial diagrammatic side view of an alternate embodiment of the plasma generator of the electrosurgical device of the present invention.

FIGS. 9 and 10 show an alternate embodiment of the plasma generator 114 including the electrode 128 supported by the handpiece 126 and at least partially disposed in the fluid flow housing 129. The electrode 128 is concentrically disposed within the inner noble gas conduit 210 having a proximal end 212 and a distal end 214 coupled to a noble gas source (not shown) by a noble gas supply conduit 216 to feed noble gas such as helium or argon to the noble gas conduit 210. A sintered conductive element 238 is disposed on the distal portion of the electrode 128 at least partially disposed within the inner noble gas conduit 210.

In use, the electrosurgical device 110 is effective and safe in various applications such as open surgery, skin resurfacing, sterilization and internal surgery.

There are two operating modes, a gentle mode and an aggressive mode. The mechanisms for energy delivered to the surgical site 118 for the two modes are different. It was found that energy is delivered either through volumetric heating or surface heating.

In volumetric heating, the energy flux is distributed within the target volume. In this mechanism, the discharge current dissipates energy in the target material.

Surface heating can be defined as heating due to hot gas flow and heating due to direct heating by the high temperature plasma stream 116 in contact with the target area 118.

In the gentle mode, a jet of hot gas is generated. Very small current is induced through the plasma stream 116, and the plasma is created in a regime of electric field induced breakdown of the gas, such as in a fluorescent lamp. Energy deposition to the patient 120 is mostly through a flux of heated gas. A small current of less than about 250 µA RMS, flows through the patient 120. It takes about 0.25 seconds for the noble gas discharge to reach a stable equilibrium flow rate of about 0.05 second in the gentle mode.

In the aggressive mode, preferred for surgical applications, a relatively high current is induced in the plasma stream 116, substantially increasing the temperature and density. As previously stated, the return current flows back to the electrosurgical generator 112 through the patient/target, and from there through the surrounding air and the surgeon holding the handpiece 126. Energy deposition to the patient 120 in this mode of operation is mostly electrical, through charged particle bombardment of the patient/target. The conducting plasma stream 116 couples the electrosurgical generator 112 to the patient 120. Peak patient/target currents as high as about 200 mA are generated. The value of this current is inversely proportional to the distance between the patient 120 and the handpiece 126.

Figure 7:
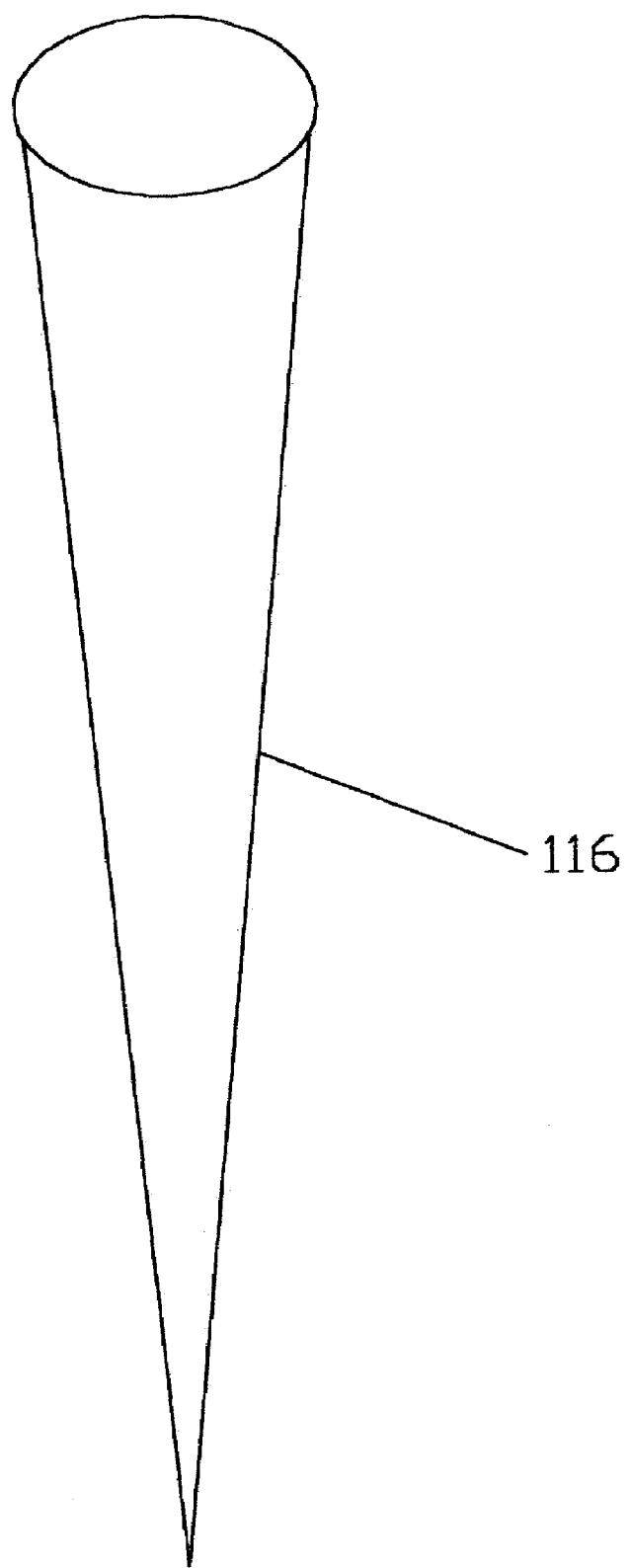
FIG. 7 depicts a plasma stream in an ambient atmosphere.
Figure 8:
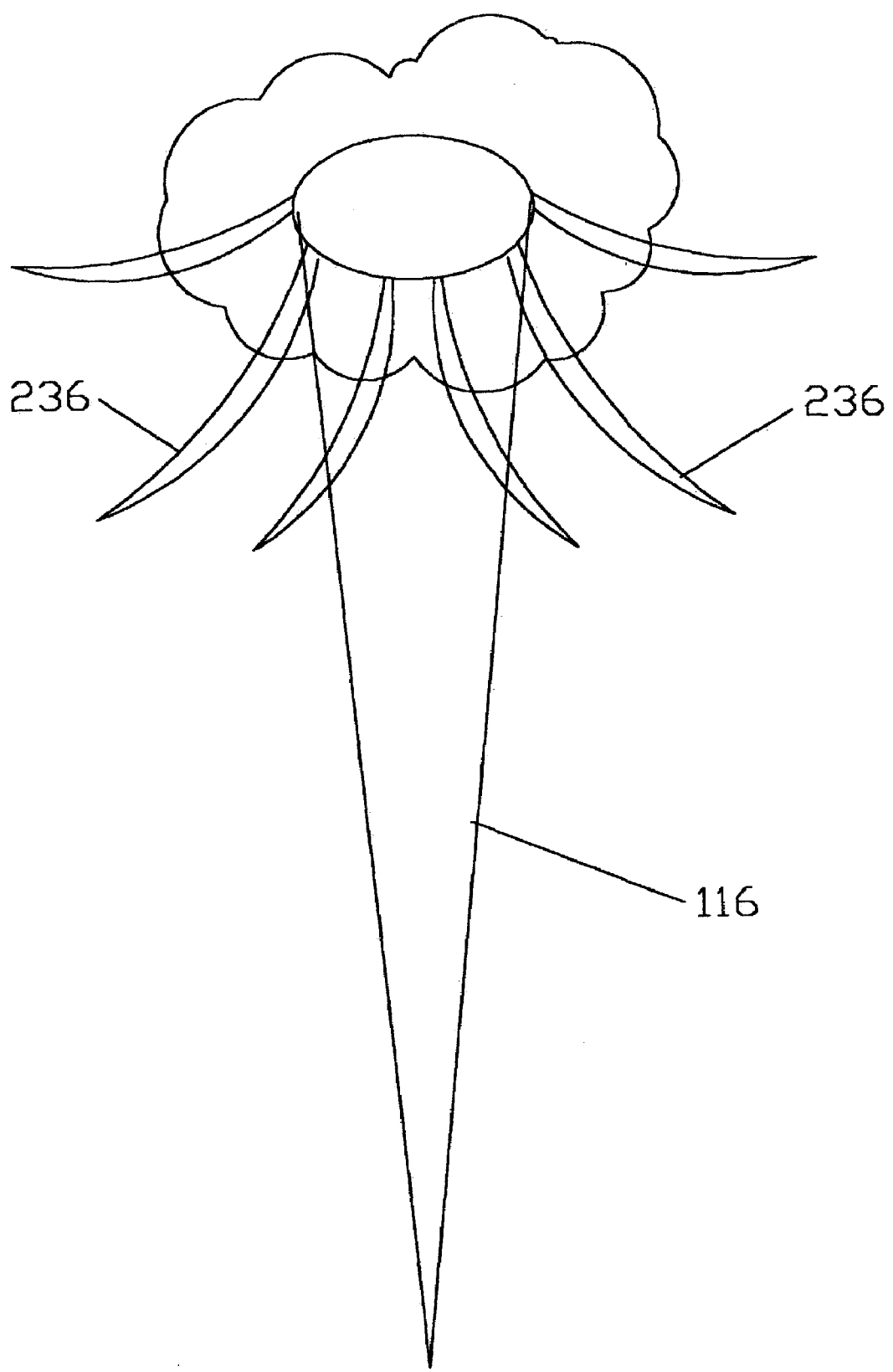
FIG. 8 depicts a plasma stream in a helium atmosphere.

The noble gas flow from the plasma generator nozzle 129 is laminar creating a stable gas flow and a focused plasma stream 116 as shown in FIGS. 6 through 8. The laminar flow protects the plasma stream 116 from penetration of oxygen and nitrogen which are electronegative and abundant in the surrounding air thereby preserving the stability of the focused plasma stream 116 of being quenched by the air or oxygen/nitrogen.

The thin, focused, plasma stream 116 acts as an extended, non-contact electrode, which delivers the current to the exposed surface of the target area 118. This primary arc induces multiple secondary sparks on a large area of the target area 118 and are capable of evaporating target tissue much like an electrosurgical ablation probe. Both the primary arc 116 and the multiple secondary sparks 236 are shown in FIG. 8. The multiple secondary sparks 236 can gradually remove material away from the primary arc 116. In other words, the area affected by the plasma generator stream is larger than the cross sectional area of the primary plasma stream 116.

The plasma stream current is a function of the drive capabilities of the electrosurgical generator 112 as well as the total impedance of the return current loop including the displacement current area. The smaller the capacitance and the conductivity from the patient 120 to the ground electrode of the transformer 124, the smaller is the current flowing through the return current circuit. The plasma stream current is limited by the generator rating or the return current path whichever is smaller.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. An electrosurgical device to generate a plasma stream for performing electrosurgery on a surgical site on a patient comprising an electrosurgical generator coupled to a electrical power source to supply power to the electrosurgical device and a plasma generator including an electrode operatively coupled to said electrosurgical generator to receive electrical energy therefrom and disposed within an inner noble gas conduit including a distal end and a proximal end to form a plasma channel coupled to a noble gas source to feed noble gas to said inner noble gas conduit such that said electrode at least partially ionizes the noble gas to generate the plasma stream to be directed to the surgical site to perform the surgical procedure, said electrosurgical device further including an intermediate electronegative gas conduit including a distal end and a proximal end disposed in surrounding relation relative to said inner noble gas conduit to cooperatively form an electronegative gas channel therebetween coupled to a gas source to feed electronegative gas to said electronegative gas channel, said distal end of said intermediate electronegative gas conduit extending beyond said distal end of said inner noble gas conduit such that the electronegative gas sustains the plasma stream.

2. The electrosurgical device of claim 1 further including an outer aspiration conduit disposed in surrounding relation relative to said intermediate electronegative gas conduit to cooperatively form an aspiration channel therebetween coupled to a negative pressure source, said negative pressure source to remove fluid and solid debris from said surgical site.

3. An electrosurgical device to generate a plasma stream for performing electrosurgery on a surgical site on a patient comprising an electrosurgical generator coupled to a electrical power source to supply power to said electrosurgical device and a plasma generator including an electrode operatively coupled to said electrosurgical generator to receive electrical energy therefrom and disposed within an inner noble gas conduit including a distal end and a proximal end to form a plasma channel coupled to a noble gas source to feed noble gas to said inner noble gas conduit such that said electrode at least partially ionizes the noble gas to generate the plasma stream to be directed to the surgical site to perform the surgical procedure, said electrosurgical device further including an outer aspiration conduit including a distal end and a proximal end disposed in surrounding coaxial relation relative to said inner noble gas conduit to cooperatively form an aspiration channel therebetween coupled to a negative pressure source, said distal end of said outer aspiration conduit extending beyond said distal end of said inner noble gas conduit to remove fluid and solid debris from the surgical site.

4. The electrosurgical device of claim 3 further an intermediate electronegative gas conduit disposed in surrounding relation relative to said noble gas conduit to cooperatively form an electronegative gas channel therebetween coupled to a gas source to feed electronegative gas to said electronegative gas channel such that said electronegative gas sustains said plasma stream.

5. An electrosurgical device to generate a plasma stream for performing electrosurgery on a surgical site on a patient comprising an electrosurgical generator coupled to a electrical power source to supply power to said electrosurgical device and a plasma generator including an electrode operatively coupled to said electrosurgical generator to receive electrical energy therefrom and disposed within an inner noble gas conduit including a distal end and a proximal end to form a plasma channel coupled to a noble gas source to feed noble gas to said inner noble gas conduit such that said electrode at least partially ionizes the noble gas to generate the plasma stream to be directed to the surgical site to perform the surgical procedure, said electrosurgical device further including an intermediate gas conduit including a distal end and a proximal end disposed in coaxial relation relative to said noble gas conduit to cooperatively form a secondary noble gas channel therebetween coupled to a noble gas source to feed noble gas to said secondary noble gas channel to form a secondary plasma stream, said distal end of said intermediate gas conduit extending beyond said distal end of said inner noble gas conduit to at least partially envelop said plasma stream to at least partially ionize the secondary plasma stream.

6. The electrosurgical device of claim 5 further including an outer aspiration conduit disposed in surrounding relation relative to said intermediate electronegative gas conduit to cooperatively form an aspiration channel therebetween coupled to a negative pressure source, said negative pressure source to remove fluid and solid debris from said surgical site.

* * * * *